United States Patent [19]

Hoffmann et al.

[11] B 3,996,367

[45] Dec. 7, 1976

[54] N,N-DIMETHYL-O-[1-METHYL-3-N-METHYLCARBAMINYL-METHYL-PYRAZOL(5)YL]-CARBAMIC ACID ESTER

[75] Inventors: Hellmut Hoffmann, Wuppertal; Ingeborg Hammann, Cologne, both of Germany

[73] Assignee: Bayer Aktiengesellschaft, Leverkusen, Germany

[22] Filed: Apr. 9, 1975

[21] Appl. No.: 566,464

[44] Published under the second Trial Voluntary Protest Program on February 3, 1976 as document No. B 566,464.

[30] Foreign Application Priority Data

Apr. 26, 1974   Germany ................... 2420360

[52] U.S. Cl. .................. 424/273; 260/310 R
[51] Int. Cl.² .................. A01N 9/22; C07D 231/20
[58] Field of Search ............... 260/310 R; 424/273

[56] References Cited
UNITED STATES PATENTS

| | | | |
|---|---|---|---|
| 2,681,915 | 6/1954 | Gysin et al. | 260/310 R |
| 3,449,502 | 6/1969 | Gubler | 424/273 |
| 3,452,043 | 6/1969 | Grauer et al. | 424/273 |
| 3,810,911 | 5/1974 | Hoffman et al. | 424/273 |

Primary Examiner—Donald B. Moyer
Attorney, Agent, or Firm—Burgess, Dinklage & Sprung

[57] ABSTRACT

N,N-dimethyl-O-[1-methyl-3-N-methylcarbaminyl-methyl-pyrazol(5)yl]-carbamic acid ester of the formula

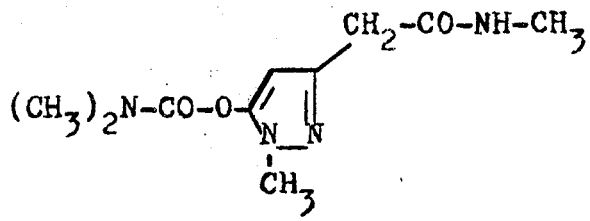

which possesses insecticidal properties.

3 Claims, No Drawings

N,N-DIMETHYL-O-[1-METHYL-3-N-METHYL-CARBAMINYL-METHYL-PYRAZOL(5)YL]-CARBAMIC ACID ESTER

The present invention relates to and has for its objects the provision of N,N-dimethyl-O-[1-methyl-3-N-methylcarbaminylmethyl-pyrazol(5)yl]-carbamic acid ester which possesses insecticidal properties, active compositions in the form of mixtures of such compound with solid and liquid dispersible carrier vehicles, and methods for producing such compound and for using such compound in a new way especially for combating pests, e.g. insects, with other and further objects becoming apparent from a study of the within specification and accompanying examples.

It is known from Swiss Patent No. 282,655 that N,N-dimethyl-O-pyrazolyl-carbamic acid esters, for example N,N-dimethyl-O-[1-phenyl-3-methyl-pyrazol(-5)yl]-carbamic acid ester (Compound A), have insecticidal properties.

The present invention provides, as a new compound, N,N-dimethyl-O-[1-methyl-3-N-methylcarbaminyl-methyl-pyrazol-(5)yl]-carbamic acid ester, which has the formula

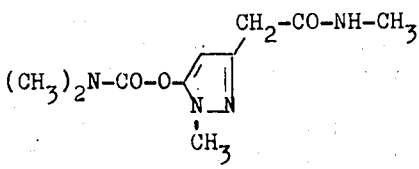

Surprisingly, N,N-dimethyl-O-[1-methyl-3-N-methylcarbaminylmethylpyrazol(5)yl]-carbamic acid ester (I) shows a better insecticidal action than the previously known N,N-dimethyl-O-[1-phenyl-3-methylpyrazol(5)yl]-carbamic acid ester of analogous structure and of the same type of action. The compound according to the invention thus represents a genuine enrichment of the art.

The invention also provides a process for the preparation of N,N-dimethyl-O-[1-methyl-3-N-methylcarbaminylmethylpyrazol(5)yl]-carbamic acid ester, in which 1-methyl-3-N-methylcarbaminylmethyl-5-hydroxy-pyrazole, of the formula

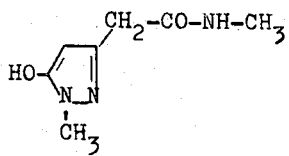

is reacted, in the presence of an acid acceptor or in the form of an alkali metal salt, alkaline earth metal salt or ammonium salt, with N,N-dimethylcarbamic acid chloride, of the formula

$(CH_3)_2N—CO—Cl$          (III), optionally in the presence of a solvent or diluent.

The course of the reaction is represented by the following equation.

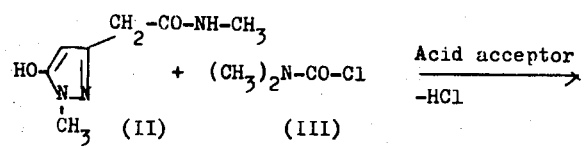

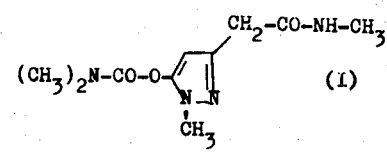

N,N-Dimethylcarbamic acid chloride, to be used as a starting material, is known from the literature and can be prepared according to known processes, as can the pyrazole derivative, which is obtainable from acetonedicarboxylic acid dimethyl ester, monomethylhydrazine and alcoholate, with subsequent reaction with monomethylamine, in accordance with the following equation:

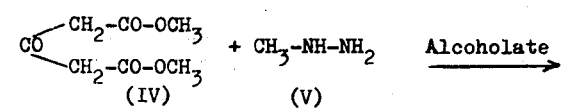

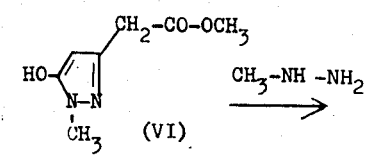

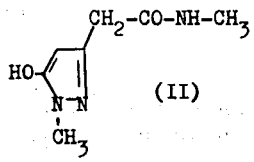

The process for the preparation of the compound (I) is preferably carried out in the presence of a suitable solvent and diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibuty ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate and potassium carbonate, sodium methylate and ethylate and potassium methylate and ethylate, have proved particularly successful, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 10° and 130°C, preferably at from 30° to 90°C.

The reaction is in general allowed to take place under normal pressure.

To carry out the process, the starting materials are in general employed in equimolar amounts. An excess of one or other reactant in general produces no essential advantages. The reaction is preferably carried out in the presence of one of the above-mentioned solvents and, if required, in the presence of an acid acceptor, at the stated temperatures. After a reaction time of 1 or more hours, in most cases at an elevated temperature, the batch is cooled and filtered and the solvent is distilled off in vacuo. The residue can be purified by recrystallization. The compound according to the invention is obtained in a crystalline form of sharp melting point.

As has already been mentioned, N,N-dimethyl-O-[1-methyl-3-N-methylcarbaminylmethylpyrazol(5)yl]-carbamic acid ester is distinguished by an excellent insecticidal activity. It is active against plant pests and combines a low phytotoxicity with a good action against sucking and biting insects.

For this reason, the compound according to the invention can be employed successfully as a pesticide in plant protection.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasins niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

When applied against pests harmful to health and pests of stored products, particularly flies and mosquitoes, the active compound is also distinguished by an outstanding residual activity on wood and clay, as well as a good stability to alkali on limed substrates.

The active compound according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compound with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethylsulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compound may be employed alone or in the form of mixtures with such solid and/or liquid dispersible carrier vehicles and/or with other known compatible active agents, especially plant protection agents, such as other insecticides, nematocides, or acaricides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compound can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Myzus test (contact action)

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Emulsifier: 1 part by weight of alkylaryl polyglycol ether

To produce a suitable preparation of active compound, 1 part by weight of the active compound was mixed with the stated amount of solvent containing the state amount of emulsifier, and the concentrate was diluted with water to the desired concentration.

Bean plants (*Vicia faba*) which had been heavily infested with the bean aphid (*Doralis fabae*) were watered with the preparation of active compound so that the preparation of active compound penetrated into the soil without wetting the leaves of the bean plants. The active compound was taken up from the soil by the bean plants and thus passed to the infested leaves.

After the specified periods of time, the degree of destruction was determined in %. 100% means that all the aphids were killed: 0% means that none of the aphids were killed.

Table 1

| | Myzus test | |
|---|---|---|
| Active compound | Active compoound concentration in % | Degree of destrustion in % after 1 day |
| (CH₃)₂N-C(O)-O-C[pyrazole ring with CH₃, phenyl] (known) (A) | 0.1<br>0.01 | 98<br>0 |
| (CH₃)₂N-CO-O-[pyrazole with CH₂-CO-NH-CH₃, CH₃] (I) | 0.1<br>0.01 | 100<br>99 |

EXAMPLE 2

Doralis test (systemic action)

Solvent: 3 parts by weight of dimethylformamide

The active compounds, the concentrations of the active compounds, the evaluation times and the results can be seen from the following table:

Table 2

| | (Doralis test/systemic) | |
|---|---|---|
| Active compound | Active compound concentration in % | Degree of destruction in % after 4 days |
| 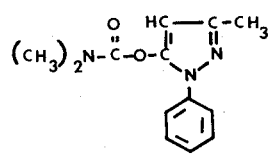 | 0.1<br>0.01 | 100<br>0 |

Table 2-continued (Doralis test/systemic)

| Active compound | Active compound concentration in % | Degree of destruction in % after 4 days |
|---|---|---|
| 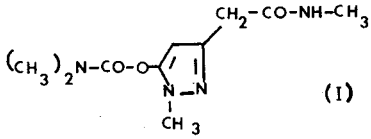 | 0.1<br>0.01 | 100<br>100 |

EXAMPLE 3 a) The preparation of the pyrazole derivative used as the starting material was effected as follows:

(i) 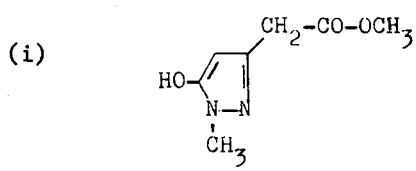 (VI)

23 G of monomethylhydrazine were added to 87 g (0.5 mole) of acetonedicarboxylic acid dimethyl ester in 200 ml of methanol, during which the reaction temperature rose to 65°C. After completion of the addition, the mixture was stirred for a further 2 hours and 0.5 mole of sodium methylate in methanol was then added. The reaction was slightly exothermic. The reaction mixture was stirred for a further 2 hours and evaporated, and the residue was dissolved in water. After acidification with glacial acetic acid, the precipitate was filtered off, dried and recrystallized from an ethyl acetate/acetonitrile mixture. 30 G (35% of theory) of 1-methyl-3-methoxycarbonylmethyl-5-hydroxypyrazole of melting point 148°C were obtained.

(ii) 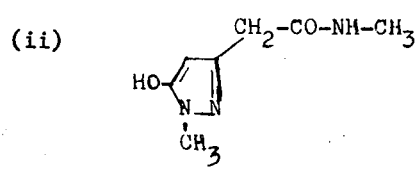 (II)

A mixture of 150 ml of an approximately 45% aqueous monomethylamine solution and 34 g of the compound (VI) prepared in (i) was left to stand for 3 days and evaporated; the residue was dissolved in a little water. After acidification with glacial acetic acid, the precipitate was filtered off and dried on clay. 17 g (50% of theory) of 1-methyl-3-N-methylcarbaminylmethyl-5-hydroxypyrazole of melting point 162°C were obtained.

b) 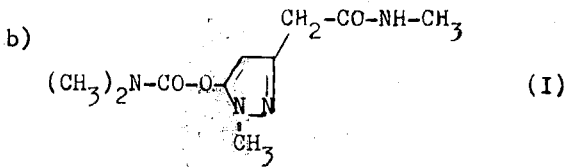 (I)

11 G of dimethylcarbamic acid chloride were added to a mixture of 17 g (0.1 mole) of 1-methyl-3-N-methylcarbaminylmethyl-5-hydroxypyrazole and 11 g of triethylamine in 200 ml of acetonitrile. The reaction mixture was heated for 6 hours under reflux, cooled and filtered, and the solvent was evaporated off in vacuo. The residue was recrystallized from ethyl acetate, giving 18 g (75% of theory) of N,N-dimethyl-O-[1-methyl-3-N-methylcarbaminylmethylpyrazol(5)yl]-carbamic acid ester of melting point 88°C.

It will be appreciated that the instant specification and examples are set forth by way of illustration and not limitation, and that various modifications and changes may be made without departing from the spirit and scope of the present invention.

What is claimed is:

1. N,N-Dimethyl-O-[1-methyl-3-N-methylcarbaminylmethyl-pyrazol(5)yl]-carbamic acid ester of the formula

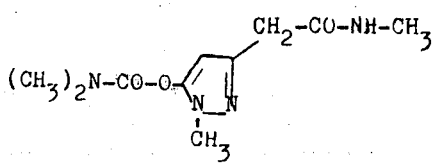

2. An insecticidal composition containing as active ingredient an insecticidally effective amount of the compound according to claim 1 in admixture with a diluent.

3. A method of combating insects which comprises applying to the insects or an insect habitat an insecticidally effective amount of the compound according to claim 1.

* * * * *